United States Patent [19]

Kotzsch et al.

[11] 4,226,793
[45] Oct. 7, 1980

[54] PROCESS FOR THE MANUFACTURE OF MONOMERIC AND OLIGOMERIC SILICIC ACID ESTERS

[75] Inventors: Hans-Joachim Kötzsch; Claus-Dietrich Seiler, both of Rheinfelden; Hans-Joachim Vahlensieck, Wehr, all of Fed. Rep. of Germany

[73] Assignee: Dynamit Nobel Aktiengesellschaft, Troisdorf, Fed. Rep. of Germany

[21] Appl. No.: 946,464

[22] Filed: Sep. 28, 1978

[30] Foreign Application Priority Data

Oct. 5, 1977 [DE] Fed. Rep. of Germany ....... 2744726

[51] Int. Cl.$^2$ .............................................. C07F 7/04
[52] U.S. Cl. .................................................. 556/470
[58] Field of Search ................................ 260/448.8 A

[56] References Cited

U.S. PATENT DOCUMENTS

| 2,484,394 | 10/1949 | van Zwet | 260/448.8 A |
| 3,985,781 | 10/1976 | Kötzsch et al. | 260/448.8 R |
| 4,060,538 | 11/1977 | Kötzsch et al. | 260/448.8 A |

*Primary Examiner*—Paul F. Shaver
*Attorney, Agent, or Firm*—Sprung, Felfe, Horn, Lynch & Kramer

[57] ABSTRACT

An improvement in a process for forming an orthosilicic acid ester or an oligomer thereof by contacting a tetrachlorosilane or higher homolog thereof with a primary alcohol, the improvement which comprises introducing the alcohol directly into a tetrachlorosilane liquid phase without said alcohol touching the gas phase and, after completion of the reaction, removing hydrogen chloride formed during the reaction from the reaction zone.

13 Claims, No Drawings

PROCESS FOR THE MANUFACTURE OF MONOMERIC AND OLIGOMERIC SILICIC ACID ESTERS

BACKGROUND OF THE INVENTION

1. Field of the Invention

This invention relates to a process for the manufacture of silicic acid esters by esterification of chlorosilanes and/or chlorosiloxanes with primary alcohols. This invention also relates to oligomerization effected simultaneously with esterification or immediately thereafter, by addition of water, to form compounds of the formula

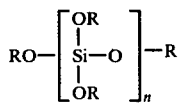

wherein
R represents an alkyl radical of 1 to 12 carbon atoms, which alkyl radical can contain a hetero atom in the chain, such as oxygen or sulfur,
n represents a whole number or, in the case of oligomeric mixtures, a fraction as well, between 1 and 10, preferably between 1 and 6.

2. Discussion of the Prior Art

It is known to form orthosilicic acid esters or their oligomeric condensation products by reacting chlorosilanes with alcohols. The known processes suffer from several drawbacks owing to the formation of a chain of by-products. These by-products appear regularly in more or less concentrated amounts. The essential side reaction prevailing is the reaction whereby developing hydrogen chloride reacts with alcohol reactant to form water, alkyl chloride and dialkyl ethers. The last two compounds pollute the hydrogen chloride being generated and make it unsuitable for the production of highly pure trichlorosilane which is useful in the field of transistors. The organic compounds contain pollutants such as methyldichlorosilane under the conditions of trichlorosilane synthesis. These pollutants cannot be readily removed from the trichlorosilane and therefore provide inferior transistor silicon when the process is conducted to form highly purified silicon.

Additionally, the water formed interferes by way of hydrolysis with the esterification reaction of the chlorosilane and forms a residue consisting of oligomeric and polymeric siloxanes which are useless for reasons of their undefined structure. These by-products represent considerable loss of material and reduce yield. Moreover, the maneuverability of the esterification reaction becomes particularly difficult at the point where oligomeric silicon esters of desired structure or of certain polymers should be produced because the water which develops in the undesired side reaction blocks the occurrence of these compounds. In doing so, undesirable polycondensates develop which cannot be separated from the desirable polycondensates and which therefore lower the quality of the end product.

Another drawback, customary with reactions of hydrogen chloride in the conventional process, occurs in the production of such silicic acid esters whose alkyl radicals contain hetero atoms such as oxygen in ether compounds. The developing hydrogen chloride acts ether-cleavage and leads to an undesirable content of organically bound chlorine within the end product. The by-products contain β-chloroethoxy groups which possess in part highly toxic properties, as is known.

As a consequence, it became desirable to provide a process for the complete esterification of tetrachlorosilane and its oligomeric homologs, which process could be conducted in such a way as to obtain the desired ester in the highest possible yield. More especially, it became desirable to provide a process which could be conducted with realization of as few pollutants as possible. In addition, it became desirable to provide a process wherein the hydrogen chloride resulting from the process would be of sufficient purity that it could be reacted with ferrosilicon or silicon to form highly pure halosilanes.

SUMMARY OF THE INVENTION

The long-felt desideratum in this field is provided by a process in accordance with the present invention whereby chlorosilanes are esterified with alcohols, the process being characterized in that the alcohols are fed directly into a chlorosilane liquid phase without making contact with the gas phase and, following completion of the reaction, the hydrogen chloride formed during the reaction is removed from the reaction zone.

In the production of orthosilicic acid esters, alcohol free of water is admixed with the chlorosilane. In the production of oligomeric silicic acids of the above-mentioned formula, water containing alcohol having a defined water content can be employed. The oligomeric silicic acid esters can also be obtained by formation of the orthosilicic acid ester initially and conversion of the orthosilicic acid ester, after separation of the hydrogen chloride, by contacting the same with a defined amount of water to effect oligomerization. The water can be added in the form of an alcohol-water mixture. The defined necessary amount of water employed is determined by the desired degree of condensation and is thus calculated accordingly. According to the invention, oligomeric silicic acid esters can be manufactured in such a way that higher homologs of silicon tetrachloride, i.e., hexachlorodisiloxane or octachlorotrisiloxane can be used as starting material and can be reacted with alcohol free of water.

In contrast to the known processes, the process of the invention has the advantage of permitting control of the reaction toward the desired product qualities, e.g., purity and degrees of polymerization of the ester, absence of by-products and residues and nearly quantitative yields. Another advantage resides in the fact that by using the procedure of the invention, the resultant hydrogen chloride is free of alkylchlorides and dialkylethers. Therefore, it does not have to be purified for further use and can be admixed directly for the reaction of silicon or ferrosilicon to form a chlorosilane.

A direct comparison of the process with known processes reveals the superiority of the inventive process, which is characterized by the virtually complete absence of side reactions. This particular absence of side reactions is surprising since, as a rule, in the endothermic development of esters according to stoichiometric conversion, hydrogen chloride is provided in particularly high quantities in the reaction zone and is present there before it escapes into the gas phase. According to the invention, the alcohol is introduced into a chlorosilane liquid phase without coming in contact with the gas phase of the reaction mixture. It is essential for the process to esterify two chlorine atoms initially and that hydrogen chloride formed be removed before the last chlorine atom is esterified. Direct esterification of all chlorine atoms without HCl removal is impossible.

Commerically, the inventive process is practiced by introducing the alcoholic components in liquid form through a floor valve or intake pipe, in some instances, by stirring the reaction mixture and therefore preventing a backflow into the intake pipe. This can be effected by calibration of the pipe. By using slightly increased pressure, at least matching the pressure of the liquid column of the reaction mixture, a backflow of the reaction mixture into the intake pipe is precluded.

Reaction temperatures need not be selected in advance of startup, since temperature will establish itself during the reaction. As a rule, the temperature drops during the reaction because the reaction is an endothermic reaction. Starting temperatures can be chosen virtually at random and are normally in the range of from $-40°$ C. to $+140°$ C. According to the inventive process, esterification between $0°$ C. and $+95°$ C. is preferred. Preferably, the esterification reaction is effected without the application of external heat. Only when producing the methyl ester, is it advantageous to work with temperatures above $+4°$ C., since orthosilicic acid tetramethyl ester solidifies at $+4°$ C.

The rate of alcohol addition and calibration of the intake pipe can also be largely picked at random. Essentially, it depends upon the capacity and output of the reflux cooler, whose function it is to cool the hydrogen chloride escaping during the reaction in order to prevent extraction of the synthesized ester. The dosage pressure of the alcohol components depends upon the counterpressure of the reaction mixture, which is disposed over the intake conduit. As stated above, the pressure of the alcohol must be at least equal to, and generally greater than, the pressure of the reaction mixture within the reaction zone upon the intake conduit. Additional pressure reaching a 10 mm water column is deemed sufficient; a higher pressure can also be used. For example, the pressure is simply produced by the level of the alcohol supply tank and/or by using a flow control valve.

The hydrogen chloride which develops during esterification remains partially dissolved within the liquid reaction product. A great portion of it escapes from the reaction zone in the gaseous form. Preferably, it is cooled in a cooling coil in order to separate out any chlorosilane or silicic acid ester. From there it can be directly diverted to another purpose.

A portion of the hydrogen chloride formed remains dissolved in the reaction product and is separated from the reaction medium after completion of the esterification reaction. This is achieved by commonly known methods, such as heating the reaction product until the boiling point is reached. Such heating can usually commence after completion of the alcohol addition, since the esterification reaction generally occurs virtually spontaneously. After the removal of the remaining hydrogen chloride from the reaction product, the product can be processed directly according to known expedients. The preferred process of distillation provides products with residual acidity of less than 6 ppm hydrolysable chloride in yields of over 96 percent.

When manufacturing oligomeric silicic acid esters with approximately 4-5 —SiO— units, i.e., ethylsilicate 40 or methylsilicate 51, according to the invention, it is unnecessary to subject the end product to a distillation or other purification. The end product results in such purity that it can be used directly as an additive or for other procedures.

The conversion can take place in the presence of solvents. The solvents useful for the conversion include those known solvents used for esterification. Solvents are particularly preferred when the esterification is being effected with higher alcohols or ether alcohols. The solvents can be used in any amount between 2 and 15 volume percent, based upon the amount of chlorosilane in the mixture. The function of the silane is to reduce the solubility of hydrogen chloride and to lower the boiling point of the raw product. Particularly contemplated solvents include hydrocarbons and chlorohydrocarbons such as hexane, heptane, isooctane, benzene, toluene, trans-dichloroethylene, trichloroethylene, perchloroethylene, etc.

Chlorosilane reactants useful in the process include, in particular, tetrachlorosilane and its higher homologs, especially identified by the formula $Cl_3Si [OSi(Cl_2)]_n Cl$, wherein n has a value between 0 and 10, preferably between 1 and 6. Examples of higher chlorosilanes include hexachlorodisiloxane, octachlorotrisiloxane and hexachlorocyclotrisiloxane.

Alcohol reactants particularly contemplated include primary alcohols such as methanol, ethanol, n-propanol, the primary butanols, pentanols, hexanols, heptanols, octanols, nonanols, decanols, undecanols and dodecanols. In addition, monoethers of glycols can be used such as cellosolve, as for example, 2-methoxyethanol, 2-ethoxyethanol, 2-butoxyethanol, diethyleneglycolmonomethyl ether, diethyleneglycolmonobutyl ether and tetraethyleneglycolmonomethyl ether. Products successfully manufactured in accordance with the invention include the methyl ester derived from a chlorosilane, which methyl ester has heretofore been formed by conventional procedures only in low yield. Other particularly desirable products produced by the described process include tetramethoxysilane, hexamethoxydisiloxane, octamethoxytrisiloxane and methylsilicate 51 (a polysilicic acid methyl ester with a 51 percent by weight $SiO_2$ content), the ethyl ethers, such as tetraethoxysilane, hexaethoxydisiloxane, ethysilicate 40 (polysilicic acid ethyl ester with 40 percent $SiO_2$ content) among others, for example, tetra-n-propylorthosilicate, tetra-n-butylorthosilicate, tetra-n-octylorthosilicate, tetra-2-ethylhexylorthosilicate, tetra-2-ethoxyethylorthosilicate and its oligomers, i.e., polysilicic acid-2-ethoxyethyl ester with $SiO_2$ content of approximately 15 percent.

In order to more fully illustrate the nature of the invention and the manner of practicing the same, the following examples are presented.

EXAMPLES

Example 1

Preparation of tetramethoxysilane from tetrachlorosilane and methanol according to the inventive process:

238 kg (1.4 k mol) of tetrachlorosilane are placed into a glazed 250 liter vessel with agitator equipped with a jacket suitable for heating and cooling, a reflux cooler (12 m$^2$) working at $-48°$ C. and a reflux condenser with a conduit for hydrogen chloride removal (for reuse), two thermometers, one each for measuring the gas phase and the liquid phase, and an alcohol container of 220 liter volume with flow control valve fitted with a discharge outlet of 8 mm in diameter, commencing 8 cm above the torispherical bottom of the reactor whose intake conduit has a declining height of approximately 1600 mm above the mound of the discharge outlet.

Over a period of 175 minutes, 179.2 kg (5.6 k mol) of methanol (free of water) is stirred into the vessel through the immersion tube at a starting temperature of 12° C. and at a constant rate of approximately 1 kg per minute, causing the spontaneous evolution of hydrogen chloride. The temperature of the liquid phase drops within a few minutes down to −19° C., the temperature of the gas phase at the same time dropping to approximately −8° C. Because the solidification point of tetramethoxysilane is +4° C., the temperature of the liquid phase in the reactor is regulated to +6° C. by cooling with water.

In the meantime, the gas phase reaches a temperature of approximately 4°–6° C. Towards the completion of methanol addition, both temperatures rise slowly to approximately 12° C. (coolant temperature approximately 14° C.). Within approximately 140 minutes after competion of the addition, the raw product is heated to its boiling point (121° C.) and drawn off for distillation into the bladder-shaped portion of a 6-plate column which uses 15 mm porcelain bridges as filament therein.

The gas chromatographic analysis of the raw product shows an amount of 98.2 percent by weight tetramethoxysilane, approximately 0.8 percent by weight hexamethoxydisiloxane and approximately 1 percent by weight trimethoxychlorsilane.

The continuous gas chromatographic analysis of the hydrogen chloride given off shows no content of methylchloride or dimethyl ether during any phase of the reaction. The portion of evaporated products amounts to approximately 0.01 percent by weight.

The distillation produces 202 kg (94.8 percent) tetramethoxysilane after a pre-run containing approximately 3 kg trimethoxychlorsilane. The boiling point is about 121° C. The residual acidity amounts to 16 ppm of chloride capable of being hydrolyzed.

All together, approximately 125 Nm$^3$ hydrogen chloride is extracted as by-products. A partial stream of the same is reacted with ferrosilicon and converted to trichlorosilane at 320° C. in a fluidized bed reactor in a conventional way. In the trichlorosilane derived in this manner no methyldichlorosilane could be traced. The semiconductor silicon extracted by thermal reduction with a hydrogen stream and epitaxy contains less than 1 ppm carbon.

Comparative Example 1

Preparation of tetramethoxysilane from tetrachlorosilane and methanol by conventional process:

47.76 kg (0.28 k mol) of tetrachlorosilane are charged into a 50 liter vessel equipped with agitator, interior heatable and coolable heat-exchange coil (0.5 m$^2$), with a reflux condenser (working at −48° C.) and gas conduit for hydrogen chloride extraction (for reuse), two thermometers, one each for measuring the gas phase and the liquid phase, and an alcohol container of 50 liter volume with a flow control valve which is equipped with a discharge outlet of 25 mm inner diameter, leading to the gas phase of the reactor.

Within 150 minutes, 35.84 kg (1.12 k mol) methanol (free of water) is dropped into the reaction mixture at a constant rate of approximately 240 g/minute while being agitated at a starting temperature of 14° C. The temperature of the liquid phase rises within a few minutes to 43° C., the temperature of the gas phase spontaneously rising to 79° C. During the methanol addition, the liquid phase is maintained at approximately 27°–32° C. by cooling with water. In the meantime, the temperature of the gas phase varies between 58° C. and 76° C. After the completion of methanol addition consuming approximately 150 minutes, the temperature is raised to the boiling point of the reaction mixture (147° C.) and the boiling raw product is drawn off for distillation using the same type of distillation vessel set forth in Example 1, supra.

The gas chromatographic analysis of the raw product shows approximately 6.4 weight percent trimethoxychlorosilane, approximately 35.4 weight percent tetramethoxy silane and approximately 58 percent oligomeric methoxysilane. The constant gas chromatographic analysis of the evolving hydrogen chloride shows amounts of methylchloride of between approximately 4.8 percent and 12.7 percent and a methanol content of approximately 0.7 weight percent during the addition of methanol. During the heat-up period, approximately 2–4 weight percent dimethylether develops. The portion of the vaporized raw product amounts to approximately 0.01 weight percent.

From an approximately 4 kg run consisting primarily of trimethoxychlorosilane, the distillation provides 10.6 kg (24.2 percent) tetramethoxychlorosilane with a residual acidity of approximately 0.8 percent of hydrolysable chloride. This renders the product unfit for use. Therefore, it must be re-distilled. Within the residue, there remains approximately 21 kg of unusable methoxypolysiloxanes with a residual acidity of 5.2 percent of chloride capable of hydrolysis.

Example 2

Preparation of tetraethoxysilane from tetrachlorosilane and ethanol according to the inventive process:

170 kg (1 k mol) tetrachlorosilane is placed into a glazed 250 liter vessel with agitator, heatable and coolable double lining, equipped with a reflux condenser working at −48° C. (12 m$^2$) and a gas conduit for hydrogen chloride extraction (for reuse), two thermometers, one each for measuring the temperature of the gas phase and the liquid phase, and an alcohol container of 220 liter volume with flow control valve whose discharge outlet leads via a T-shaped pipe, capable of being locked, toward the bottom of the reaction vessel. The discharge pipe has an inner diameter of 8 mm and is situated above the bottom valve of the reactor by a distance of approximately 2000 mm.

Within approximately 180 minutes, 184 kg (4 k mol) ethanol (free of water) is introduced from the container toward the bottom of the vessel at a constant rate of addition of 1 kg per minute employing a starting temperature of 15° C. Spontaneous and violent development of hydrogen chloride takes place. The temperature of the liquid phase, as well as the gas phase, drops within a few minutes to −11° C. and stays at approximately that temperature over a period of time. The temperature rises to approximately +2° C. during approximately the last third of the period of the reaction time. After completion of the addition, the reaction mixture is brought to its boiling point (168° C.) over a time span of approximately 140 minutes. Distillation is effected in accordance with Example 1.

Gas chromatographic analysis of the raw product shows 97.8 weight percent tetraethoxysilane, 1.4 weight percent hexaethoxydisiloxane and approximately 0.7 weight percent triethyoxychlorosilane. The constant gas chromatographic analysis of the escaping hydrogen chloride shows no ethylchloride or diethylether content during any phase of the reaction. The portion of the evaporated product amounts to less than 0.1 weight percent. After a run containing approximately 1.8 kg triethoxychlorosilane, the distillation produces 200.6 kg (96.5 weight percent) tetraethoxysilane. The boiling point is about 168° C. The residual acidity is about 6 ppm of hydrolysable chloride.

All together, approximately 90 Nm³ of hydrogen chloride is obtained as by-product. The trichlorosilane produced in a manner similar to that of Example 1 shows no traces of methyldichlorosilane.

Comparative Example 2

Preparation of tetraethoxysilane from the tetrachlorosilane and ethanol according to conventional procedures:

34 kg (200 mol) tetrachlorosilane are placed into a vessel similar to that described in Comparative Example 1. Within 120 minutes, 38.8 kg (800 mol) ethanol (free of water) are added dropwise with agitation at a constant rate of approximately 300 grams per minute at a starting temperature of 15° C. The temperaure of the liquid phase rises within a few minutes to 31° C., while the temperature of the gas phase rises to 64° C. During the ethanol addition, the liquid phase is maintained at a temperature of 21° C. by cooling with water. In the meantime, within the gas phase the temperature varies between 52° C. and 64° C. Within 150 minutes after completion of the ethanol addition, the raw material is brought to a boil (179° C.) and distillation is effected in the manner of Comparative Example 1.

The gas chromatographic analysis of the raw product shows amounts of approximately 9.2 percent triethoxychlorosilane, approximately 65.6 percent tetraethoxysilane and approximately 25 percent of oligomeric ethoxysilane. During the addition of ethanol, the constant gas chromatographic analysis of the escaping hydrogen chloride shows amounts of ethyl chloride between approximately 1 percent and approximately 5.4 percent and ethanol of approximately 0.6 percent. During the heat-up period, approximately 2 percent diethyl ether occurs. The portion of the evaporated product amounts to less than 0.01 percent.

In addition to the 6 kg triethoxychlorosilane produced from the run, the distillation produces 21.3 kg (51.2 weight percent) tetraethoxysilane with a residual acidity of approximately 0.3 percent of hydrolyzable chloride, requiring the product to be re-distilled in order to make it usable. In the residue, there remains approximately 11.8 kg of non-usable ethoxypolysiloxanes whose residual acidity is 1.9 weight percent of chloride capable of being hydrolyzed.

All together, approximately 17 Nm³ of hydrogen chloride is obtained as by-product. Approximately 0.9 percent methyldichlorosilane can be traced within the obtained trichlorosilane produced similar to Example 1. From the trichlorosilane, a silicon quality is obtained by thermal reduction with a hydrogen stream and epitaxy which contains approximately 412 ppm carbon. It is, therefore, un-usable as semi-conductor silicon.

Example 3

Preparation of tetra-2-methoxyethoxysilane from tetrachlorosilane and 2-methoxy ethanol according to the invention process:

Similar to Example 1, 102 kg (600 mol) of tetrachlorosilane are used. Within approximately 180 minutes, 183 kg (2.4 mol) of 2-methoxyethanol (free of water) are stirred in at a constant rate of 1 kg per minute whereby hydrogen chloride escapes in the form of gas. The temperature of both the liquid as well as gas phase drops slowly to 12° C. and remains for some time between 12° and 14° C. It finally rises to about 22° C. over the last third period of the reaction time. Within approximately 70 minutes after completion of the addition, the raw product is heated to 104° C. and 12 kg perchloroethylene is stirred in while the temperature is raised to the boiling point (146° C.). The boiling raw product is drawn off into the cavity of a 6-neck column with an expansion metal lining (Kloss-column) for distillation.

The gas chromatographic analysis of the raw product shows partially pure tetra-2-methoxyethoxy silane in addition to approximately 6 percent perchloroethylene. Some pollutants in the pre- and post-run area are considered possible (approximately 0.002 weight percent). The constant gas chromatographic analysis of the escaping hydrogen chloride shows no signs of foreign matter during any phase of the reaction.

The distillation produces 197 kg (97.5 percent) tetra-2-methoxyethoxy silane whose boiling point is 132° C. (1 Torr). The residual acidity is about 6 ppm of chloride capable of being hydrolyzed. The total chlorine content amounts to 44 ppm.

Comparative Example 3

Preparation of tetra-2-methoxyethoxysilane from tetrachlorosilane and 2-methoxy ehtanol according to conventional procedure:

In a manner similar to Comparative Example 1, 20.4 kg (120 mol) of tetrachlorosilane is employed. Within approximately 120 minutes, 36.6 kg (480 mol) of 2-methoxy ethanol (free of water) is stirred in while agitated at a constant rate. The rate of alcohol addition is 300 g/minute and a starting temperature of 19° C. is maintained. The temperature of the liquid phase rises within minutes to 36° C., while the temperature of the gas phase rises to 58° C. During the addition of methylglycol, a temperature of 20° C. is maintained by use of external water coolant. Meanwhile, the temperature in the gas phase ranges between 45° and 58° C. Within approximately 70 minutes after completion of the addition, the temperature is raised to 104° C., 3 kg perchloroethylene is stirred in while the temperature is raised to the boiling point (152° C.) and then distilled in a manner similar to that of Example 3.

Besides approximately 7.5 weight percent perchloroethylene, the gas chromatographic analysis of the raw products shows approximately 4.1 weight percent tri-2-methoxyethoxychlorosilane, approximately 2.1 weight percent tri-2-methoxyethoxy-2-chloroethoxysilane, approximately 70.8 weight percent tetra-2-methoxyethoxysilane and approximately 15 weight percent of oligomeric 2-methoxyethoxysiloxanes, in addition to small quantities of other impurities in the pre-run area.

The constant gas chromatographic analysis of the escaping hydrogen chloride shows amounts of methyl chloride of between approximately 1 weight percent and 4.7 weight percent, amounts of dichloroethane between approximately 0.7 and 3.0 weight percent and amounts of 2-methoxyethanol of approximately 0.5 weight percent. Besides a 3.1 kg pre-run, consisting mainly of tri-2-methoxyethoxychlorosilane and tri-2-methoxyethoxy-2-chlorethoxysilane, the distillation provides 26.2 kg (65.6 weight percent) tetra-2-methoxyethoxysilane of residual acidity of about 800 ppm of hydrolyzable chloride and with a total chlorine content of 0.3 percent which cannot be separated by distillation. The product is, therefore, useless. Within the residue there remains about 8 kg non-usable 2-methoxyethoxypolysiloxanes of residual acidity of 0.6 weight percent of hydrolyzable chloride and a total chlorine content of approximately 2 weight percent.

Example 4

Preparation of tetra-2-ethoxyethoxysilane from tetrachlorosilane and 2-ethoxyethanol:

In a manner similar to Example 1, 88.4 kg (520 mol) of tetrachlorosilane and 20 kg perchloroethylene are used. Within approximately 180 minutes, 187 kg (2.08 k mol) of 2-ethoxyethanol (free of water) are stirred in through an immersion tube at a constant rate of approximately 1 kg per minute at a starting temperature of 20° C., whereby hydrogen chloride escapes in gas form. The temperatures of both liquid and gas phase drop slowly to 12° C., remain there in the range of 12°–14° C. for some time, and finally rise during the last third of the reaction time slowly to 20° C. Within 70 minutes after completion of the addition, the product is brought to a 154° C. boiling point and then distilled in a similar fashion to that of Example 3.

The gas chromatographic analysis of the raw product shows virtually pure tetra-2-ethoxyethoxysilane in addition to about 8 weight percent perchloroethylene. Several minor amounts of impurity within the pre-and post-run area are conceivable (approximately 0.002 weight percent).

The constant gas chromatographic analysis of the escaping hydrogen chloride does not show any foreign matter. The distillation produces 196 kg (98 weight percent) tetra-2-ethoxyethoxysilane of boiling point of about 142° C. (1 Torr). The residual acidity ranges between 4 ppm or less of hydrolyzable chloride. The total chlorine content amounts to 30 ppm.

Example 5

Preparation of hexamethoxydisiloxane from hexachlorodisiloxane and methanol:

2850 g (10 mol) of hexachlorodisiloxane and 200 ml trichloroethylene are placed into a 4 liter multiple neck vessel with agitator capable of being heated or cooled by thermostats equipped with a reflux condenser working at −42° C. (0.2 m$^2$) with a gas conduit leading to a container containing a lime solution, two thermometers, one for measuring the temperature of the gas phase, the other for measuring the temperature of the liquid phase, and a dropping funnel with flow control valve whose discharge outlet is situated under the surface of the liquid ending in a discharge opening with 1 mm inner diameter. Within approximately 95 minutes, 1920 g (60 mol) of methanol (free of water) are stirred in through the immersion tube at a constant rate of about 20 g/min. at a starting temperature of 24° C., whereby hydrogen chloride develops in the form of gas. The temperature of the liquid phase drops within minutes to −23° C., while the temperature of the gas phase drops simultaneously to −2° C. Only in the last third of the time period of the methanol addition does the temperature rise slowly in both phases to approximately 12° C. Within 70 minutes after completion of the addition, ebullition is achieved at 127° C. A final distillation produces 2530 g (98.2 percent) hexamethoxydisiloxane of boiling point 81° C. (2 Torr) in addition to 200 ml trichloroethylene.

$D_4^{20}$ 1.123; $n_D^{20}$ 1.3813; melting point $< -70°$ C.;

| Elemental analysis: | C | H | Si |
|---|---|---|---|
| Projected ($C_6H_{18}O_7Si_2$): | 27.9 percent | 7.0 percent | 21.7 percent |
| Actual result: | 27.8 percent | 7.2 percent | 21.7 percent |

Example 6

Preparation of octamethoxytrisiloxane from octachlorotrisiloxane and methanol:

In a manner similar to Example 5, 2000 g (5 mol) of octachlorotrisiloxane and 200 ml isooctane are placed into the reactor. Within 60 minutes, 1280 g (40 mol) of methanol (free of water) are stirred in. The change in temperature during the reaction develops along the lines of that in Example 5. Within 60 minutes after completion of the methanol addition, the reaction mixture is brought to a boil (142° C.). In addition to 200 ml isooctane, the final distillation produces 1712 g (94.3 percent) octamethoxytrisiloxane at boiling point 116° C. (2 Torr).

$D_4^{20}$ 1.163; $n_D^{20}$ 1.3866; melting point $< -70°$ C.;

| Elemental analysis: | C | H | Si |
|---|---|---|---|
| Projected ($C_8H_{24}O_{10}Si_3$): | 26.3 percent | 6.6 percent | 23.1 percent |
| Actual result: | 26.4 percent | 6.8 percent | 23.0 percent |

Example 7

Preparation of methyl silicate 51 (polysilicic acid methyl ester with 51 weight percent SiO$_2$ content) by reaction of tetrachlorosilane, methanol and water according to the inventive process:

The procedure of Example 1 is followed, except that the raw product is not distilled after heating. Instead it is combined with nitrogen and admixed with 2 kg methanol at 104° C. using an immersion tube and the mixture is boiled until neutralization is effected over a period of two hours at reflux. Thereafter, the product is cooled down under nitrogen to 40° C. and 18.6 kg (1.05 k mol) of distilled water is added thereto through an immersion tube over a period of approximately 10 minutes. It is stirred for two hours and methanol is separated in a distillation retort, as described in Example 1, at 50 Torr and at a temperature of 65° C. The product is condensed in a reflux condenser working at −45° C. (methanol yield: 64.6 kg comparable to a 95 weight percent yield. 162.8 kg methyl silicate 51 are obtained from the distillation chamber. This represents a yield of approximately 99 percent. The residual acidity is less than 4 ppm hydrolyzable chloride.

$D_4^{20}$ 1.160; Flashpoint 45° C.; Viscosity 7.7 cP (20° C.); Decomposition temperature approximately 150° C.

| Elemental analysis: | C | H | SiO$_2$ |
|---|---|---|---|
| Projected ($C_{10}H_{30}O_{13}Si_4$): | 25.6 percent | 6.4 percent | 51.1 percent |
| Actual result: | 25.4 percent | 6.5 percent | 51.0 percent |

Without any further purification, the product is ready for industrial use in known fashion, for instance in the production of reflective layers on glass tubes for electronic-ray oscillographs, as binder for sand employed in the formation of molds, and for the production of zinc-dust pigments.

Example 8

Preparation of ethyl silicate 40 (polysilicic acid ethyl ester of 40 weight percent $SiO_2$ content) from tetrachlorosilane, ethanol and water according to the claimed process:

2550 kg (15 k mol) of tetrachlorosilane are placed into a 4 m$^3$ vessel with agitator, equipped with a jacket capable of heating and cooling, a reflux cooler working at −45° C. (30 m$^2$) and a reflux condenser and a gas conduit for hydrogen chloride (for re-use), two thermometers, one for measurement of the temperature of the gas phase and the other for measurement of the temperature of the liquid phase, an alcohol container of 4 m$^3$ volume with flow control valve whose discharge system is equipped with a discharge outlet of 25 mm inner diameter situated about 25 cm above the tovispherical bottom of the reactor and whose declining height is approximately 8 m above the mound of the discharge outlet.

Within approximately 240 minutes, 2530 kg (55 k mol) ethanol (free of water) are stirred in through the immersion tube from the alcohol container at a starting temperature of +6° C. The addition of the first 500 kg is done at a rate of approximately 8 kg per minute, whereby the temperatures of the liquid and gas phase drop down to approximately −9° C. in the reactor. Thereafter, the ethanol feed is raised to 12-13 kg per minute, whereby inner temperatures begin to drop still further. These temperatures rise during the last third of the time period of the ethanol addition to approximately 18° C. Within 180 minutes after completion of the ethanol addition, the product is heated until constant boiling is obtained (about 167° C.). After heating, the raw product is contacted with nitrogen and is mixed with a solution of 205 kg (11.4 k mol) of distilled water in 500 kg ethanol. It is stirred for three hours at a temperature of approximately 70° C. The raw product is then transferred into a distillation zone equipped with a single neck and ethanol is separated at 30 Torr and 78° C. and condensed in a reflux condenser working at −45° C. There is recovered approximately 99 percent of the ethanol (1285 kg) which is capable of reuse.

The product is withdrawn from the distillation zone through a column filled with zinc granules. 2200 kg ethylsilicate 40 is obtained, comparable to a yield of approximately 98 percent.

The pH is determined to be approximately 7.2 utilizing a universal indicator (Merck).

A hydrolysis test of 200 ml in a Dewar-container shows a rise in temperature from 20° C. to 39.8° C. in 312 seconds when stirred with a mixture of 160 ml ethanol and 40 ml hydrochloric acid. The synthesized ethyl silicate 40 has a density of $D.4^{20} = 1.052$, a flashpoint of 46° C., and a viscosity of 4.7 cP (20° C.).

| Elemental analysis: | C | H | $SiO_2$ |
|---|---|---|---|
| Projected ($C_{20}H_{50}O_{13}Si_4$): | 39.3 percent | 8.4 percent | 39.3 percent |
| Projected ($C_{24}H_{60}O_{16}Si_5$): | 38.7 percent | 8.1 percent | 40.3 percent |

| Elemental analysis: | C | H | $SiO_2$ |
|---|---|---|---|
| Actual result: | 38.9 percent | 8.2 percent | 39.9 percent |

The actual product is suitable for industrial use without further purification. It can be used in the manufacture of zinc dust pigments employed as anti-corrosive coating agents such as against salt water and other aggressive atmospheres. It could also be used as a binder for sand, such as in the formation of molds.

Constant gas chromatographic analysis of the hydrogen chloride escaping during the reaction shows no traces of ethyl chloride or diethyl ether during any phase of the reaction. The portion of evaporated product amounts to less than 0.01 weight percent. In total, about 1200 Nm$^3$ hydrogen chloride is obtained as by-product. The hydrogen chloride is suitable for reuse.

A partial stream of the hydrogen chloride is reused by contacting the same with ferrosilicon at 320° C. in a fluidized bed reactor and converted to trichlorosilane. Within the trichlorosilane obtained, there are no traces of methyldichlorosilane. The semi-conductor silicon obtained by treatment of the same with hydrogen chloride and epitaxy shows less than 1 ppm carbon.

Comparative Example 4

Preparation of ethyl silicate 40 (polysilicic acid ethyl ester with 40 weight percent $SiO_2$ content) from tetrachlorosilane, ethanol and water according to the conventional process:

2550 kg (15 k mol) of tetrachlorosilane are placed in a 4 cubic meter vessel equipped with agitator as mentioned in Example 8, equipped with an intake conduit of 40 mm diameter terminating in an alcohol container on one end and, on the other, a point above the liquid phase of the tetrachlorosilane, i.e., into the gas phase of the reactor. In a similar way, 2622 kg (approximately 57 k mol) ethanol are added dropwise through an intake conduit into the installation. The temperature of the liquid phase rises to 27° C. The temperature of the gas phase rises to about 40° C. After completion of the addition, the reaction mass is brought to a boil (approximately 168° C.). After boiling, the raw product is contacted with nitrogen and mixed with a solution of 163.8 kg (9.1 k mol) of distilled water and 400 kg ethanol. When the ethanol is separated, 1080 kg (89.7 percent yield) of desired product is recovered. The lost portion of ethanol, in comparison to Example 8, amounts to 197 kg.

Neutralization is effected in a manner similar to Example 8 using higher zinc content. There is also produced 2200 kg of usable ethyl silicate 40 of pH 7.1. The hydrolysis test is effected within 370 seconds.

The constant gas chromatographic analysis of the hydrogen chloride given off during the reaction shows approximately 2.9 weight percent ethyl chloride and 0.6 weight percent diethyl ether in addition to 1.8 weight percent ethanol. The portion of the evaporated product amounts to 0.01 weight percent. All together, approximately 1200 Nm$^3$ hydrogen chloride are obtained as by-product for reuse. In the trichlorosilane derived in a manner analogous to Example 8, approximately 0.7 weight percent methyldichlorosilane can be found. When converted to silicon by thermal reduction with hydrogen and epitaxy, the resultant silicon contains 300 ppm carbon, which renders it useless as semi-conductor silicon.

What is claimed is:

1. In a process for the manufacture of an orthosilicic acid ester or an oligomer thereof wherein a tetrachlorosilane or a higher homolog thereof is contacted with a primary alcohol, in some instances with the addition of water, the improvement which comprises introducing the alcohol directly into a tetrachlorosilane or higher homolog thereof liquid phase without said alcohol touching the gas phase and, after completion of the reaction, removing any residual hydrogen chloride from the reaction zone.

2. A process according to claim 1 wherein the alcohol is introduced into the liquid phase at a slightly elevated pressure.

3. A process according to claims 1 or 2 wherein the reaction is effected without the application of external heat.

4. A process according to claim 1 wherein the alcohol employed is one which is free of water.

5. A process according to claim 1 wherein water is added to the reaction mixture without said water touching the gas phase and the reaction mixture is heated to a temperature between 40° and 100° C. whereby there is obtained an oligomeric silicic acid ester.

6. A process according to claim 5 wherein an inret gas is additionally added to the reaction mixture.

7. A process according to claim 6 wherein said inert gas is nitrogen.

8. A process according to claim 5 wherein the alcohol added to the reaction mixture is in admixture with an amount of water corresponding to the desired degree of oligomerization.

9. A process according to claim 1 wherein the silane reactant has the formula $$Cl_3Si[O\text{-}Si(Cl_2)]_nCl$$

wherein
n is a value between 1 and 10 and the reaction is effected employing alcohol free of water.

10. A process according to claim 9 wherein n is a value between 1 and 6.

11. A process according to claim 1 wherein the reaction is effected in the presence of a hydrocarbon or chlorohydrocarbon solvent.

12. A process according to claim 1 wherein the reaction is completed before removal of any residual hydrogen chloride from the reaction zone.

13. A process according to claim 1 wherein all of the chlorine atoms of the tetrachlorosilane are esterified prior to hydrogen chloride removal.

* * * * *